United States Patent
Juvinall et al.

(10) Patent No.: US 7,480,040 B2
(45) Date of Patent: Jan. 20, 2009

(54) METHOD AND APPARATUS FOR INSPECTING CONTAINER SIDEWALL CONTOUR

(75) Inventors: John W. Juvinall, Ottawa Lake, MI (US); Brian A. Langenderfer, Sylvania, OH (US)

(73) Assignee: Owens-Brockway Glass Container Inc., Perrysburg, OH (US)

( * ) Notice: Subject to any disclaimer, the term of this patent is extended or adjusted under 35 U.S.C. 154(b) by 428 days.

(21) Appl. No.: 11/285,269

(22) Filed: Nov. 22, 2005

(65) Prior Publication Data

US 2007/0115466 A1   May 24, 2007

(51) Int. Cl.
*G01N 21/00* (2006.01)
(52) U.S. Cl. .................. 356/239.4; 356/239.7
(58) Field of Classification Search ... 356/239.1–240.1, 356/426–428, 601; 250/223 B, 559.19–559.24, 250/578.1, 559.28
See application file for complete search history.

(56) References Cited

U.S. PATENT DOCUMENTS

| | | | |
|---|---|---|---|
| 3,343,673 A | 9/1967 | Thacker et al. | |
| 4,171,481 A | 10/1979 | Mima et al. | |
| 4,209,387 A | 6/1980 | Schef | |
| 4,553,217 A | 11/1985 | Daudt et al. | |
| 5,291,271 A | 3/1994 | Juvinall et al. | |
| 5,844,677 A | 12/1998 | Dimmick, Sr. et al. | |
| 6,025,910 A | 2/2000 | Lucas | |
| 6,369,889 B1 | 4/2002 | Olschewski | |
| 6,806,459 B1 | 10/2004 | Ringlien et al. | |

FOREIGN PATENT DOCUMENTS

| | | |
|---|---|---|
| DE | 29907762 U1 | 11/1999 |
| EP | 1318391 A1 | 6/2003 |
| GB | 2195178 A | 3/1988 |
| WO | WO2006/017041 A1 | 2/2006 |
| WO | WO2006/052320 | 5/2006 |

*Primary Examiner*—Gregory J Toatley, Jr.
*Assistant Examiner*—Tri T Ton

(57) ABSTRACT

Apparatus for inspecting contour of a container sidewall includes at least one light source for directing light energy onto the container sidewall and at least one light sensor disposed to receive light energy from the light source reflected from the container sidewall. The light sensor is responsive to such reflected light energy to provide signals indicative of position of the container sidewall relative to the sensor at at least two locations on the container sidewall spaced from each other in the direction of the container axis. An information processor is responsive to such signals to determine contour of the container sidewall as a function of sidewall positions at such locations. The at least two locations on the container sidewall preferably are nominally aligned with each other in a direction parallel to the container axis. One of the locations on the container sidewall preferably is adjacent to the container shoulder or the container heel, and another of the locations is on the container sidewall between the container shoulder and the container heel.

19 Claims, 3 Drawing Sheets

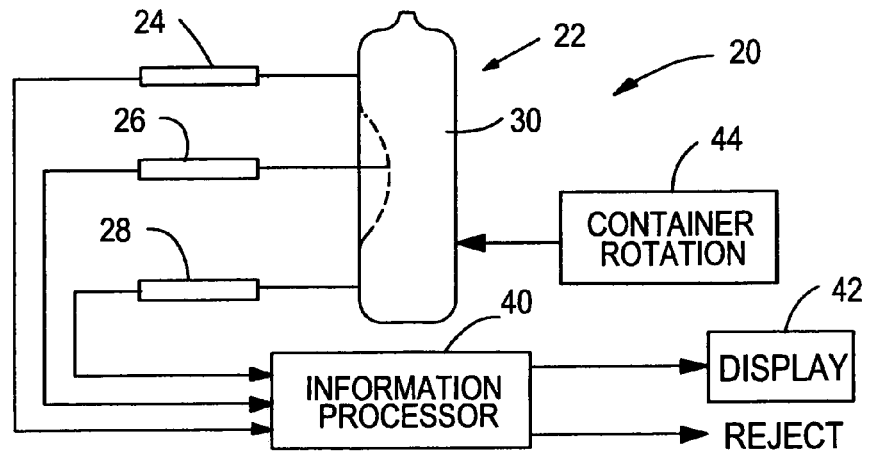
FIG.1
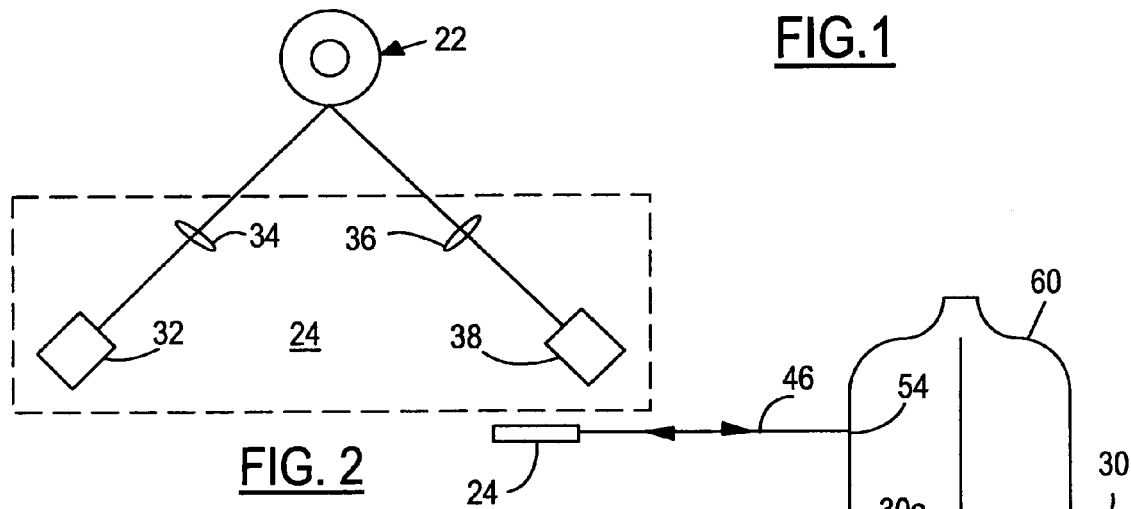
FIG. 2
FIG. 3
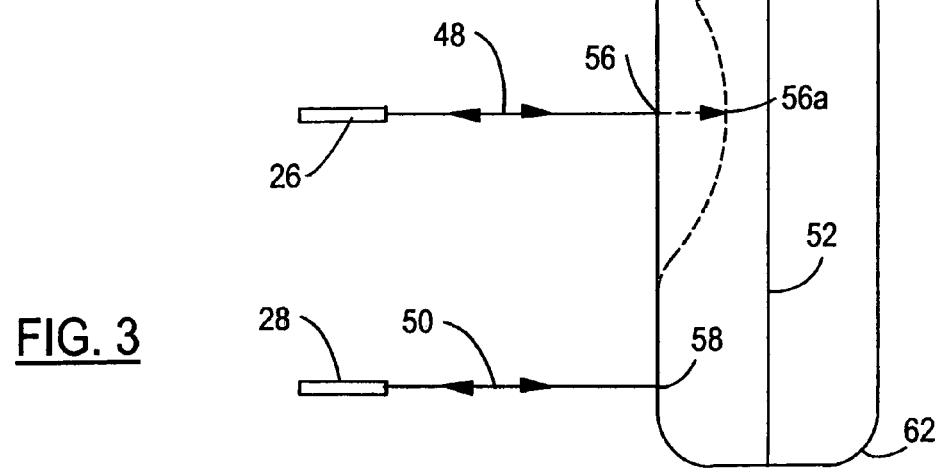

METHOD AND APPARATUS FOR INSPECTING CONTAINER SIDEWALL CONTOUR

The present disclosure relates to inspection of sidewall uniformity in containers, particularly glass containers, and more particularly to a method and apparatus for identifying bulges or sunken sections in the container sidewall.

BACKGROUND AND SUMMARY OF THE DISCLOSURE

U.S. Pat. No. 5,291,271 discloses an apparatus and method for electro-optically measuring the thickness of a container wall. A light source directs a light beam onto the outer surface of a container at an angle such that a portion of the light beam is reflected from the outer surface, and a portion is refracted into the container wall, reflected from the inner wall surface and then re-emerges from the outer wall surface. A lens system is disposed between a light sensor and the container wall for focusing light energy reflected from the outer and inner wall surfaces onto the sensor. The container is rotated around an axis, and information processing electronics are responsive to the light energy incident on the sensor for scanning the sensor at increments of container rotation and determining wall thickness of the container between the inner and outer wall surfaces as a function of the separation between the points of incidence of the reflected light energy on the sensor. Light energy reflected from the outer surface of the container wall also provides information concerning wall contour around the container as a function of container rotation at the location at which the light energy is incident on and reflected from the wall surface.

The present disclosure embodies a number of aspects that can be implemented separately from or in combination with each other.

Apparatus for inspecting contour of a container sidewall, in accordance with one aspect of the present disclosure, includes at least one light source for directing light energy onto the container sidewall and at least one light sensor disposed to receive light energy from the light source reflected from the container sidewall. The light sensor is responsive to such reflected light energy to provide signals indicative of position of the container sidewall relative to the sensor at at least two locations on the container sidewall spaced from each other in the direction of the container axis. An information processor is responsive to such signals to determine contour of the container sidewall in the direction of the container axis as a function of sidewall positions at such locations. The at least two locations on the container sidewall preferably are nominally aligned with each other in a direction parallel to the container axis. One of the locations on the container sidewall preferably is adjacent to the container shoulder or the container heel, and another of the locations is on the container sidewall between the container shoulder and the container heel.

In the preferred embodiments of the disclosure, the at least one light sensor provides signals indicative of position of the container sidewall relative to the sensor at at least three locations on the container sidewall spaced from each other in the direction of the axis of the container. The information processor preferably detects variations in contour at the container sidewall as a function of the departure of the sidewall position at one of the three locations from a line between the sidewall positions at the other two of the three locations. Such other two of the three locations preferably are respectively adjacent to a heel and a shoulder of the container, while the one location preferably is between the container heel and shoulder. The container preferably is rotated around an axis, and the first, second and third locations preferably are nominally aligned with each other in a direction parallel to such axis. The sensors may comprise individual sensors disposed to receive light energy reflected from the container sidewall at the three sidewall locations, or an area array sensor disposed to receive light energy reflected from all three of the sidewall locations.

BRIEF DESCRIPTION OF THE DRAWINGS

The disclosure, together with additional objects, features, advantages and aspects thereof, will best be understood from the following description, the appended claims and the accompanying drawings, in which:

FIG. 1 is a schematic diagram of an apparatus for inspecting contour of a container sidewall in accordance with one exemplary embodiment of the disclosure;

FIG. 2 is a top plan view schematic diagram of the apparatus of FIG. 1;

FIG. 3 is a graphic illustration of operation of the apparatus of FIG. 1 and 2;

DETAILED DESCRIPTION OF PREFERRED EMBODIMENTS

Figure 4:
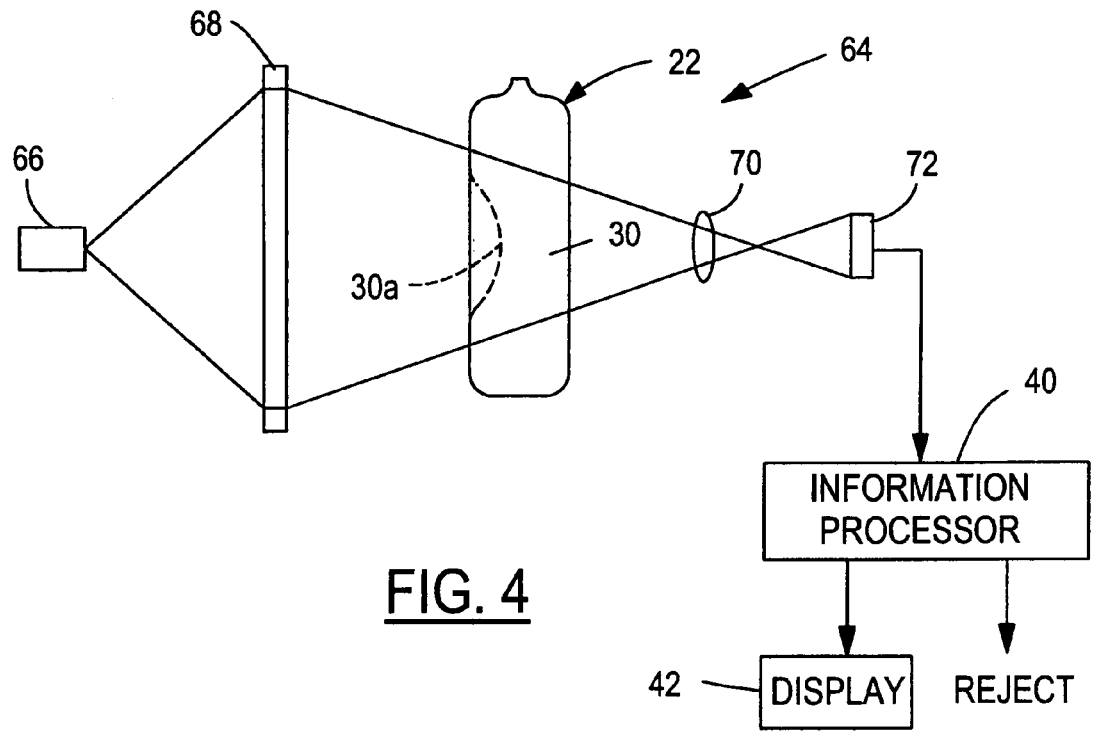
FIG. 4 is a schematic diagram of an apparatus for inspecting container sidewall contour in accordance with another exemplary embodiment of the present disclosure.

FIGS. 1 and 2 illustrate an apparatus 20 for inspecting sidewall contour of a container 22 in accordance with one exemplary embodiment of the present disclosure. Apparatus 20 includes at least one electro-optical subassembly or probe 24, and preferably three electro-optical probes 24, 26, 28 disposed to direct light energy onto and receive light energy reflected from the sidewall 30 of container 22. Probe 24 includes a light source 32 for directing light energy onto the outer surface of container sidewall 30, preferably through a lens 34, and a light sensor 38 positioned to receive light energy reflected from the outer surface of the container sidewall, preferably through a lens 36. Probes 26,28 preferably are identical to probe 24. Light source 32 and sensor 38 preferably are part of a probe subassembly; however, light source 32 and sensor 38 could be comprised of separate components. Sensors 38 of probes 24-28 are connected to an information processor 40 that determines container sidewall contour from the sensor inputs and provides an output to a suitable display 42. Information processor 40 also may provide output to a suitable reject mechanism for rejecting containers having an undesirable sidewall contour.

A container rotation mechanism 44 preferably rotates container 22 around an axis of rotation (52 in FIG. 3) as the container sidewall is inspected by probes 24-28. Container rotation mechanism 44 may comprise any suitable device, such as a drive roller coupled to a suitable drive motor for holding container 22 against back-up rollers or the like while rotating the container around an axis of rotation. Such axis of rotation preferably is coincident with the axis of the container. By way of example only, suitable systems for bringing containers 22 into position for inspection, rotating the containers in turn during the inspection operation, and removing the containers following inspection are illustrated in U.S. Pat. Nos. 4,378,493 and 6,581,751.

Referring to FIG. 3, probe 24 directs light energy onto container sidewall 30 and receives reflected light energy from a surface, preferably the outer surface, of the container sidewall in an optical plane 46. Likewise, probes 26 and 28 direct light energy onto the container sidewall and receive light energy reflected from a surface, preferably the outer surface, of the container sidewall in respective optical planes 48, 50. Planes 46, 48, 50 preferably are parallel to each other and perpendicular to container axis of rotation 52, although this need not necessarily be the case. The light energy in plane 46 is incident on and reflected from the outer surface of the container sidewall at a location 54. Likewise, the light energy in plane 48 is incident on and reflected from the container sidewall at a location 56, and the light energy in plane 50 is incident on and reflected from the container sidewall at a location 58. Location 54 preferably is adjacent to the container shoulder 60, which is accurately round due to the manner in which the container is molded. Likewise, location 58 preferably is adjacent to the container heel 62, which is accurately round due to the manner in which the container is molded. Location 56 maybe at any desired position between locations 54, 58, such as half-way between locations 54, 58 as illustrated in FIG. 3. Locations 54, 56, 58 preferably are spaced from each other in the direction of axis 52, and most preferably are nominally aligned with each other along a line parallel to axis 52. By the term "nominally" it is meant that, if container sidewall 30 is cylindrical and coaxial with axis 30, locations 54, 56 and 58 would lie along the surface of the cylinder and be aligned with each other along a line parallel to axis 52. On the other hand, if sidewall 30 is oblique to axis 52, or if sidewall 30 is sunken as at 30a so that location 56 is at 56a, locations 54, 56a, 58 would no longer be aligned with each other in a direction parallel to axis 52.

Light sensors 38 (FIG. 2) provide output signals to information processor 40 as a function of the position of the container sidewall relative to the light sensors at each of the locations 54, 56, 58. Information processor 40 preferably determines the contour of container sidewall 30 in the direction of axis 52 as a function of the departure of the sidewall positioned at location 56 from a line between the sidewall positions at locations 54 and 58. In other words, the sidewall positions at locations 54, 58 are employed by information processor 40 (FIG. 1) to establish a reference to which the sidewall position at location 56 is compared. FIG. 3 illustrates in phantom a sunken sidewall 30a, for which the sidewall positioned at location 56a will depart significantly from a reference line between the sidewall positions at locations 54 and 58. A sunken sidewall 30a may result in rejection of the container. As a modification to the embodiment of FIGS. 1-3, only one of the probes 24, 28 can be used to establish a reference to which the sidewall position output of probe 26 is compared. As another modification, additional probes could be provided between probes 24, 28.

In the embodiment of FIGS. 1-3, each of the three (or more) probes 24, 26, 28 may comprise optical thickness gauges of the type disclosed in above-noted U.S. Pat. No. 5,291,271, in which reflections from the outside surface of the container are monitored to determine container sidewall contour as described above. Sensors 38 preferably are scanned at increments of container rotation to develop a sidewall contour profile entirely around the container. Such increments of container rotation may be equal angular increments of container rotation or equal time increments as the container is rotated at constant angular velocity, for example. A combination of these techniques can be employed during acceleration and deceleration of container rotation to increase inspection speed.

Figure 5:
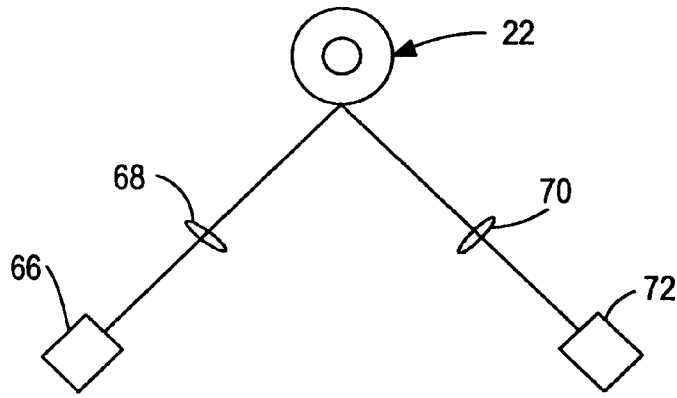
FIG. 5 is a top plan schematic diagram of the apparatus illustrated in FIG. 4.
Figure 6:
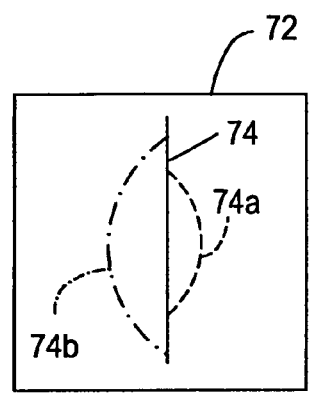
FIG. 6 is a graphic illustration of container sidewall contour inspected with the apparatus of FIGS. 4 and 5.

FIGS. 4-6 illustrate an apparatus 64 for inspecting container sidewall contour in accordance with another exemplary embodiment of the disclosure. A light source 66 and a lens 68 direct a line-shaped light beam onto the outer surface of container sidewall 30. This line-shaped light beam has a long dimension parallel to the axis of rotation of container 22 and a narrow dimension radial to such axis at the line of incidence on the container sidewall. Light energy reflected from the container sidewall is directed by a lens 70 onto a light sensor 72. In this embodiment, light sensor 72 preferably comprises an area array sensor (FIG. 6) that receives the entire reflected image of the light source. This image may comprise a line-shaped image 74 for example when the container sidewall has no bulged or sunken areas. On the other hand, a sunken area 30a (FIG. 4) may produce a contoured image 74a (FIG. 6), whereas a bulged sidewall may produce a contoured image 74b. As in the embodiment of FIGS. 1-2, sidewall contour is determined as a function of a comparison between one or more sidewall positions at locations along the mid portion of the image with sidewall positions at locations at the upper and lower portions of the image.

Figure 7:
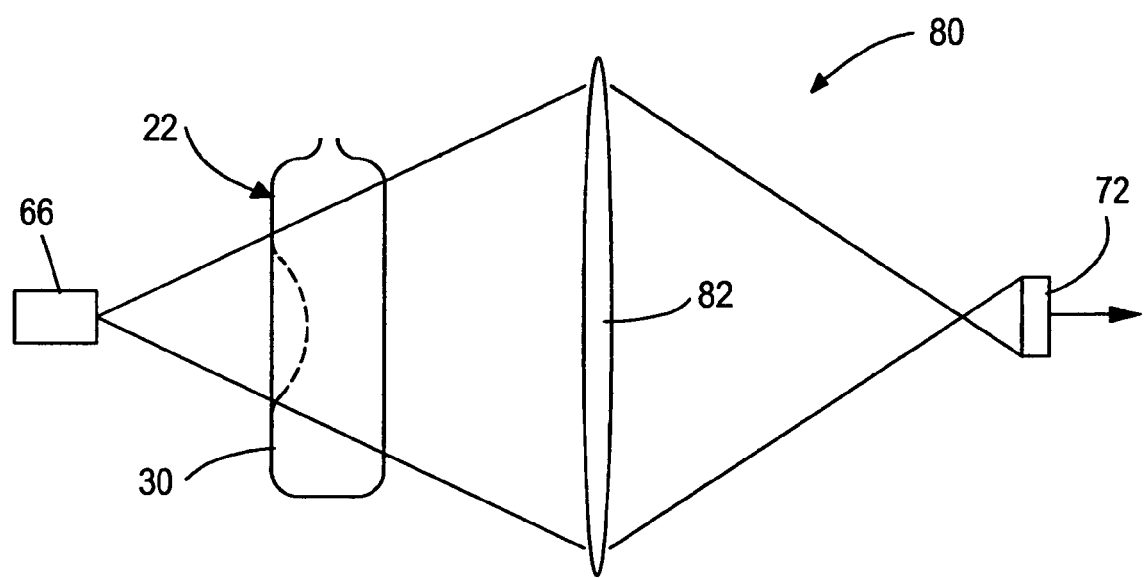
FIG. 7 is a schematic diagram of an apparatus for inspecting container sidewall contour in accordance with a further exemplary embodiment of the disclosure.

FIG. 7 illustrates an apparatus 80 as a modification to apparatus 64 of FIGS. 4-6. Light source 66 again generates a line-shaped light beam that is reflected from the outer surface of container sidewall 30, and a focusing lens 82 is positioned between container 22 and sensor 72 to direct the reflected light energy onto the surface of the sensor. The image at the sensor again is a line parallel to the container axis, while a bulge or a sink will distort this linear image as illustrated in FIG. 6.

There thus have been disclosed an apparatus and method for inspecting the contour of a container sidewall. The disclosure has been presented in conjunction with a number of exemplary embodiments, and various additional modifications and variations have been described. Other modifications and variations readily will suggest themselves to persons of ordinary skill in the art in view of the foregoing discussion. The disclosure is intended to embrace all such modifications and variations as fall within the spirit and broad scope of the appended claims.

The invention claimed is:

1. Apparatus for inspecting contour of a container having a sidewall and an axis, which includes:
   at least one light source for directing light energy onto a container sidewall,
   at least one light sensor disposed to receive light energy from said at least one light source reflected from the container sidewall, and responsive to such reflected light energy to provide signals indicative of position of the container sidewall relative to said sensor at at least two locations on the container sidewall spaced from each other in the direction of said axis, and
   an information processor responsive to said signals to determine contour of the container sidewall in the direction of said axis as a function of sidewall positions at said at least two locations,
   wherein said at least one sensor is responsive to said reflected light energy to provide signals indicative of position of the container sidewall relative to said sensor at a first location adjacent to the container shoulder, a second location adjacent to the container heel and a third location between said first and second locations, and wherein said information processor determines contour of the container sidewall as a function of departure of sidewall third location from a line between sidewall positions at said first and second locations.

2. The apparatus set forth in claim 1 wherein said first, second and third locations are nominally aligned with each other in a direction parallel to the container axis.

3. The apparatus set forth in claim 2 wherein said at least one light source and said at least one light sensor include three light sources and associated sensors respectively positioned to direct light energy onto and receive reflected light energy from the container sidewall at said three locations respectively.

4. The apparatus set forth in claim 3 wherein each said light source is such that, at each said location on the container sidewall, light energy is received and reflected in a plane perpendicular to the container axis.

5. The apparatus set forth in claim 2 wherein said light source directs a line-shaped light beam onto the container axis having a long dimension parallel to said axis and a short dimension radial to said axis, and wherein said sensor includes an area array sensor for receiving portions of said line-shaped light beam reflected from the container sidewall.

6. The apparatus set forth in claim 1 wherein said at least one light source and said at least one sensor include at least two light sources and associated sensors respectively positioned to direct light energy onto and receive light energy reflected from said one of said locations and said another of said locations.

7. The apparatus set forth in claim 6 wherein each said light source is such that, at each said location on the container sidewall, light energy is received and reflected in a plane perpendicular to the container axis.

8. The apparatus set forth in claim 1 including means for rotating the container around its axis, and wherein said information processor is adapted to determine container sidewall contour at increments of container rotation around said axis.

9. Apparatus for inspecting contour of a container sidewall, which includes:
at least one light source for directing light energy onto a container sidewall,
at least one light sensor disposed to receive light energy from said at least one source reflected from the container sidewall, and responsive to such reflected light energy to provide signals indicative of position of the container sidewall relative to said sensor at at least three locations on the container sidewall spaced from each other in the direction of an axis of the container, and
an information processor responsive to said signals for detecting variations in contour at the container sidewall, said information processor being constructed to determine contour of the container sidewall as a function of departure of sidewall position at one of said three locations from a line between sidewall positions at the other two of said three locations.

10. The apparatus set forth in claim 9 wherein said other two of said three locations are on the container sidewall respectively adjacent to a heel and a shoulder of the container, and wherein said one location is between said other two locations.

11. The apparatus set forth in claim 10 including means for rotating the container around an axis, and wherein said first, second and third locations are nominally aligned with each other in a direction parallel to said axis.

12. The apparatus set forth in claim 11 wherein said at least one light source and said at least one light sensor include three light sources and associated sensors respectively positioned to direct light energy onto and receive light energy reflected from the container sidewall at said three locations respectively.

13. The apparatus set forth in claim 12 wherein each said light source is such that, at each said location on the container sidewall, light energy is received and reflected in a plane perpendicular to the container axis.

14. The apparatus set forth in claim 11 wherein said light source directs a line-shaped light beam onto the container axis having a long dimension parallel to said axis and a short dimension radial to said axis, and wherein said sensor includes an area array sensor for receiving portions of said line-shaped light beam reflected from the container sidewall.

15. Apparatus for inspecting contour of a container sidewall, which includes:
at least one light source for directing light energy onto a container sidewall as the container is rotated around an axis,
at least one light sensor disposed to receive light energy from said at least one light source reflected from an outside surface of the container sidewall, and responsive to such reflected light energy to provide a signal indicative of position of the container sidewall relative to said sensor, and
an information processor responsive to said signal for determining contour of the container sidewall in the direction of said axis as the container is rotated around said axis,
wherein said at least one sensor is responsive to said reflected light energy to provide signals indicative of position of the container sidewall relative to said sensor at a first location adjacent to the container shoulder, a second location adjacent to the container heel and a third location between said first and second locations, and
wherein said information processor determines contour of the container sidewall as a function of departure of sidewall position at said third location from a line between sidewall positions at said first and second locations.

16. The apparatus set forth in claim 15 wherein said at least one light source and said at least one sensor include at least two light sources and associated sensors respectively positioned to direct light energy out and receive light energy from said one of said locations and said another of said locations.

17. The apparatus set forth in claim 15 wherein said first, second and third locations are nominally aligned with each other in a direction parallel to the said axis.

18. A method of inspecting contour of a container side wall having a shoulder and a heel, which includes the steps of:
(a) rotating the container around an axis,
(b) directing light energy onto the container sidewall at at least a first location adjacent to the container shoulder, a second location adjacent to the container heel, and a third location between said first and second locations,
(c) directing light energy reflected from the container sidewall at at least said first, second and third locations onto at least one light sensor to provide signals indicative of position of the container sidewall at said first, second and third locations relative to said at least one sensor, and
(d) determining sidewall contour of the container as a function of departure of sidewall positioned at said third location from a line between sidewall positions at said first and second locations.

19. The method set forth in claim 18 wherein said first, second and third locations are nominally aligned with each other in a direction parallel to said axis.

* * * * *